(12) United States Patent
Paul et al.

(10) Patent No.: US 10,995,310 B2
(45) Date of Patent: May 4, 2021

(54) BIOMANUFACTURING APPARATUS

(71) Applicant: Global Life Sciences Solutions USA LLC, Marlborough, MA (US)

(72) Inventors: Praveen Paul, Bangalore (IN); Manoj Ramakrishna, Bangalore (IN); Anoop Bhargav, Bangalore (IN); Haresh Digambar Patil, Bangalore (IN); Sebastian John, Bangalore (IN); Manish Uddhaorao Choudhary, Bangalore (IN); Pradeep Kumar, Bangalore (IN); Nivedita Phadke, Bangalore (IN)

(73) Assignee: Global Life Sciences Solutions USA LLC, Marlborough, MA (US)

(*) Notice: Subject to any disclaimer, the term of this patent is extended or adjusted under 35 U.S.C. 154(b) by 451 days.

(21) Appl. No.: 15/755,087

(22) PCT Filed: Aug. 25, 2016

(86) PCT No.: PCT/EP2016/070077
§ 371 (c)(1),
(2) Date: Feb. 25, 2018

(87) PCT Pub. No.: WO2017/032831
PCT Pub. Date: Mar. 2, 2017

(65) Prior Publication Data
US 2018/0251715 A1    Sep. 6, 2018

(30) Foreign Application Priority Data

Aug. 25, 2015  (IN) ............................ 2632/DEL/2015
Oct. 19, 2015  (GB) ...................................... 1518426
Aug. 16, 2016  (IN) .............................. 201611027824

(51) Int. Cl.
*C12M 3/06*     (2006.01)
*C12M 1/00*     (2006.01)
(Continued)

(52) U.S. Cl.
CPC ............ *C12M 27/16* (2013.01); *C12M 21/04* (2013.01); *C12M 23/14* (2013.01); *C12M 23/26* (2013.01);
(Continued)

(58) Field of Classification Search
CPC ... C12M 41/14; C12M 27/16; B01L 2200/025
See application file for complete search history.

(56) References Cited

U.S. PATENT DOCUMENTS

| 5,882,918 A | 3/1999 | Goffe |
| 6,544,788 B2 | 4/2003 | Singh |

(Continued)

FOREIGN PATENT DOCUMENTS

| CN | 2213019 Y | 11/1995 |
| CN | 204125462 U | 1/2015 |

(Continued)

OTHER PUBLICATIONS

Japanese Office Action for JP Application No. 2018-510087 dated Jun. 22, 2020 (14 pages with English translation).

(Continued)

*Primary Examiner* — Jonathan M Hurst
(74) *Attorney, Agent, or Firm* — Eversheds Sutherland (US) LLP

(57) ABSTRACT

Disclosed is biomanufacturing apparatus 1 comprising a housing 20 including top 22 and bottom 24 faces which allow stacking of plural housings, an access door 25 at a front side of the housing, a substantially enclosed bioreactor chamber 30 inside the housing accessible via the door, and a further substantially enclosed region 36 inside the housing (Continued)

containing electrical parts and/or electronic control components, the chamber 30 including: a tray 40 for supporting a bioreactor, a tray support 45 including a mechanism 44,47 for rocking the tray in use; the tray support further including a load cell (41) to determine changes in the mass load on the tray.

17 Claims, 9 Drawing Sheets

(51) Int. Cl.
  *C12M 1/107* (2006.01)
  *C12M 1/34* (2006.01)
(52) U.S. Cl.
  CPC ............ *C12M 29/10* (2013.01); *C12M 41/12* (2013.01); *C12M 41/14* (2013.01)

(56) References Cited

U.S. PATENT DOCUMENTS

| | | | |
|---|---|---|---|
| 9,109,193 B2 | 8/2015 | Galliher et al. | |
| 9,428,724 B2 | 8/2016 | Fricking | |
| 9,738,863 B2 | 8/2017 | Andersson et al. | |
| 2002/0140324 A1* | 10/2002 | Butts | C12M 41/14 312/209 |
| 2003/0036192 A1 | 2/2003 | Singh | |
| 2004/0114316 A1* | 6/2004 | Carter | B01L 1/02 361/679.29 |
| 2009/0017011 A1 | 1/2009 | Alitalo et al. | |
| 2009/0111179 A1* | 4/2009 | Hata | C12M 23/14 435/394 |
| 2011/0315783 A1* | 12/2011 | Baker | C12M 41/14 236/3 |
| 2012/0258441 A1* | 10/2012 | Gebauer | C12M 23/14 435/3 |
| 2015/0082898 A1* | 3/2015 | Ohkoshi | G01L 1/10 73/778 |

FOREIGN PATENT DOCUMENTS

| | | |
|---|---|---|
| EP | 2607474 A1 | 6/2013 |
| JP | H09-264802 A | 10/1997 |
| JP | 2003-093040 A | 4/2003 |
| JP | 2004-141036 A | 5/2004 |
| JP | 2006-166746 A | 6/2006 |
| JP | 2006-204186 A | 8/2006 |
| JP | 2007-312676 A | 12/2007 |
| JP | 2008-067822 A | 3/2008 |
| JP | 2010-098996 A | 5/2010 |
| JP | 2010-158203 A | 7/2010 |
| JP | 2011-052994 A | 3/2011 |
| JP | 2012-055827 A | 3/2012 |
| JP | 2015-121645 A | 7/2015 |
| KR | 2008-0052597 A | 6/2008 |
| WO | 2011078773 A1 | 6/2011 |
| WO | 2013135817 A1 | 9/2013 |
| WO | 2015048712 A2 | 4/2015 |
| WO | 2017032831 A1 | 3/2017 |

OTHER PUBLICATIONS

Sawaguchi et al., "New Bioreactor System for Ligament and Tendon Tissue Engineering," Journal of Japanese Society of Clinical Biomechanics, 2005, 26-33.

International Search Report and the Written Opinion of the International Searching Authority, or the Declaration from International Appl. No. PCT/EP2016/070077, dated Nov. 9, 2016.

Great Britain Search Report from GB Appl. No. GB1518426.0, dated Jul. 26, 2016.

Celltainer Biotech, "Cell-tainer single-use bioreactor for cell cultures—CM2SCEU/CM2SCUS", celltainer.com, [online], Available from: http://celltainer.com/wp-content/uploads/2015/01/cell-culture.pdf [Accessed Jul. 22, 2016] See particularly System Specifications.

Chinese Office Action for CN Application No. 201680062270.2 dated Nov. 12, 2020 (25 pages with English translation).

* cited by examiner

BIOMANUFACTURING APPARATUS

FIELD OF THE INVENTION

The present invention relates to biomanufacturing apparatus, for example for cell culturing. In particular, the invention relates to bioreactor apparatus in the form of single instruments, and plural instruments arranged into a biomanufacturing system for optimising the usage of laboratory and cell culturing space for biomanufacturing.

BACKGROUND OF THE INVENTION

Cell culture, for example the culture of mammalian, bacterial or fungal cells, may be carried out to harvest the living cells for therapeutic purposes and/or to harvest biomolecules, such as proteins or chemicals (e.g. pharmaceuticals) produced by the cells. As used herein, the term "biomolecule" can mean any molecule, such as a protein, peptide, nucleic acid, metabolite, antigen, chemical or biopharmaceutical that is produced by a cell or a virus. Herein, the term biomanufacturing is intended to encompass the culturing or multiplication of cells, and the production of biomolecules. The term bioreactor is intended to encompass a generally enclosed volume capable of being used for biomanufacturing.

The cells are generally grown in large scale (10,000 to 25,000 litre capacity) bioreactors which are sterilisable vessels designed to provide the necessary nutrients and environmental conditions required for cell growth and expansion. Conventional bioreactors have glass or metal growth chambers which can be sterilized and then inoculated with selected cells for subsequent culture and expansion. Media within the growth chambers are often agitated or stirred by the use of mechanical or magnetic impellers to improve aeration, nutrient dispersal and waste removal.

In recent years, there has been a move towards 'single use' bioreactors which offer smaller batch sizes, greater production flexibility, ease of use, reduced capital cost investment and reduced risk of cross-contamination. These systems can also improve the efficiency of aeration, feeding and waste removal to increase cell densities and product yields. Examples include WAVE™ bags (GE Healthcare) mounted on rocking platforms for mixing, to the introduction of stirred-tank single-use vessels such as those available from Xcellerex Inc (GE Healthcare). With the advent of 'personalised medicine', autologous cell therapies requiring many small batches of cells to treat patients with unique cell therapies has become important.

Manufacturing facilities, such as tissue culture laboratories, for the production of cells and biomolecules, have traditionally been custom designed and carried out in clean environments to reduce the risk of contamination. Such facilities are costly to run and maintain and also to modify if priorities or work demands change. Work stations for maintaining or harvesting the cells within the bioreactors require a specific 'footprint' which occupies a significant floor space in the culture laboratory. As the workstations spend much of their time unattended, while the cells are growing in the bioreactors, the laboratory space is not efficiently or effectively used.

An improvement is proposed in WO 2014122307, wherein the laboratory space required for cell culture is reduced by the provision of customised workstations and storage bays for bioreactors, on which, conventional WAVE type bioreactors and ancillary equipment can be supported. Large supporting frameworks are required for that equipment.

U.S. Pat. No. 6,475,776 is an example of an incubator for cell culture dishes, which has a single incubator housing and multiple shelves, however this type of equipment is not suitable for housing bioreactors.

What is needed is the ability to stack multiple bioreactors one on top of another, closely spaced side by side, in a system that is simple to load, operate and maintain. Ideally such bioreactors should be capable of tradition fed batch manufacturing where cells are cultured typically over 7 to 21 days, as well as perfusion type manufacturing where cells can be cultured for longer periods, but waste products are continually or regularly removed, and biomolecules may be harvested. On top of that, one of the important parameters that needs to be is measured during the entire cell expansion process is the weight of the cell culture. This parameter serves as an input for various application steps like step-wise cell expansion, continuous cell expansion, media fill, perfusion flow, calibration of feed & harvest pumps, temperature control and pH control. It is therefore a very important requirement for the weight measurement system to have a very good accuracy and sensitivity specification. A cell culture instrument which has a weight measuring load cells mounted on each foot of the instrument is known commercially. This is not an ideal way of mounting the load cells because the entire weight of the instrument rests on the load cells. Therefore, the dead weight acting on the load cells are very high (depending on the instrument weigh) which affects the overall accuracy and sensitivity. Also since the load cells are mounted on the instrument feet, there is a significant change in the reading of the load cells when they are subjected to even a slight side force. This is not acceptable since it results in error in the load cell readings.

An ideal weight measurement system is therefore one which carries as little dead weight as possible and is also isolated from the instrument feet so that there is no impact on the readings when there is a disturbance to the instrument, and instruments can then be stacked one on top of another.

SUMMARY OF THE INVENTION

The invention provides an arrangement according to claim 1 having preferred features defined by claims dependent on claim 1.

The invention extends to any combination of features disclosed herein, whether or not such a combination is mentioned explicitly herein. Further, where two or more features are mentioned in combination, it is intended that such features may be claimed separately without extending the scope of the invention.

BRIEF DESCRIPTION OF THE DRAWINGS

The invention can be put into effect in numerous ways, illustrative embodiments of which are described below with reference to the drawings, wherein:

The invention, together with its objects and the advantages thereof, may be understood better by reference to the following description taken in conjunction with the accompanying drawings, in which like reference numerals identify like elements in the Figures.

Referring to FIG. 1a there is shown biomanufacturing apparatus 1 including a generally self-contained instrument 10 which includes a generally cuboid or box-shaped housing 20 having generally flat upper and bottom sides 22 and 24. The bottom side includes four adjustable height feet 26, only two of which are visible in FIG. 1a. The box shaped housing allows stacking of plural instruments to form a biomanufacturing system. In practice, for convenience, the stack will be two or three high on a benchtop 5, as schematically illustrated in FIG. 1b, although there is no reason why the stack could not be higher. The instrument also includes a door 25, shown open and cut away for in order to shown the remaining parts of the instrument more clearly. The door is hinged at hinges 28 to the front vertical edge of the housing, so that it opens about a vertical hinge axis to expose or enclose an insulated chamber 30 inside the housing 20. The chamber 30 is sealed when the door is closed by an elastomeric seal 32 extending around the whole periphery of the inner face of the door and cooperating with a seal face 31 extending in a complementary manner around the front edges of the housing 20. No light enters the chamber 30 when the door 25 is closed. This negates light effects on the cell culture.

Figure 1:
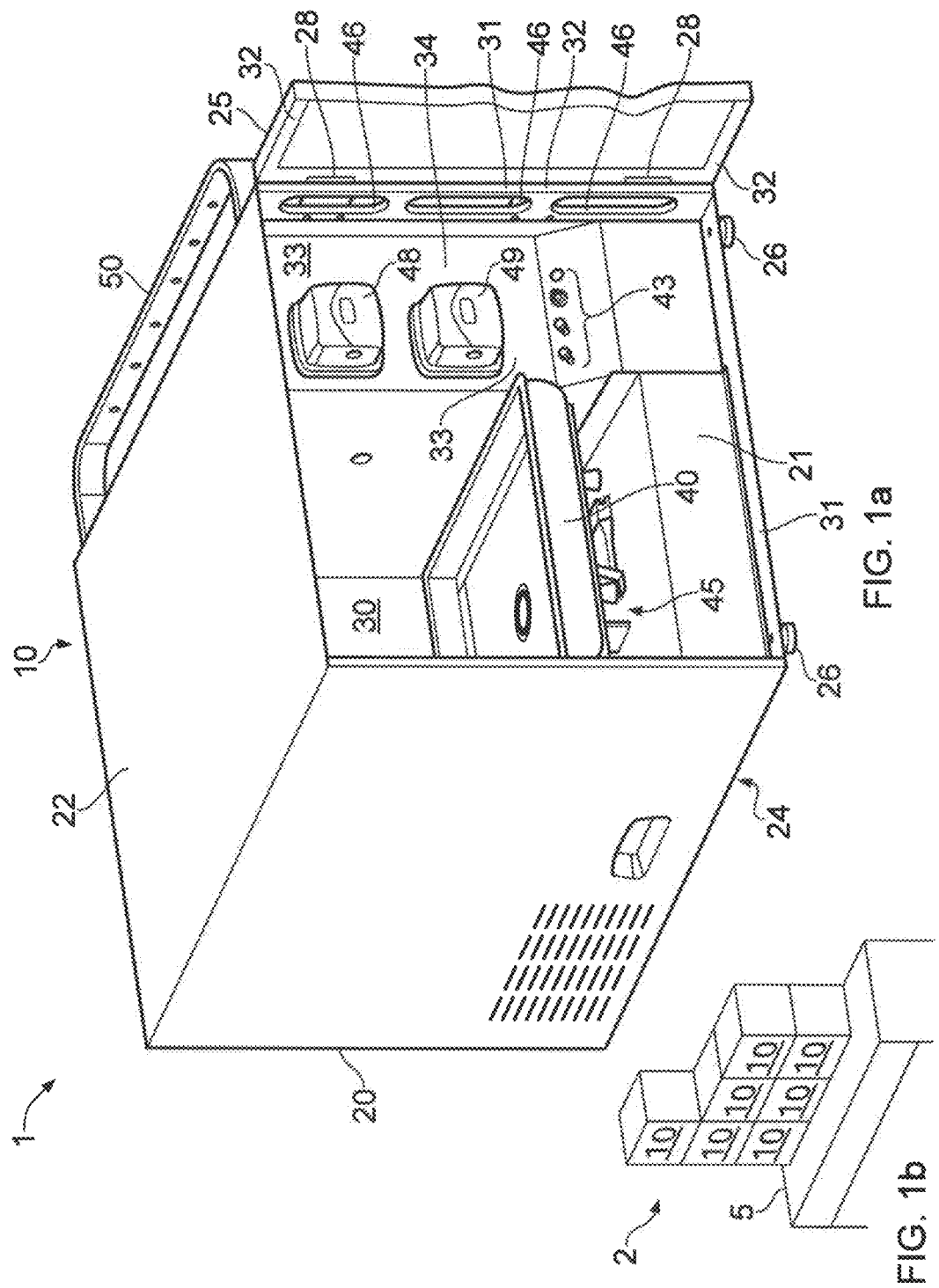
FIG. 1a shows a pictorial view of an embodiment of biomanufacturing apparatus.
FIG. 1b shows the apparatus of FIG. 1a stacked to form a biomanufacturing system 2.

The chamber 30 has a main chamber 35 and an antechamber 33 leading to the main chamber 35. The main chamber includes a bioreactor tray 40, supported by a rocking tray support 45 described in more detail below. The rocking mechanism is protected by a cover plate 21. The antechamber 33 includes a panel 34 supporting two peristaltic pumps only the fluid handling heads 48 and 49 of which extend into the antechamber 33, the electrical parts of which are behind the panel 34. The panel also includes connections 43 described in more detail below. The antechamber 33 includes openings 46 defining a route for conduits extending to an external storage area which includes a bag hanging rack 50.

Figure 2:
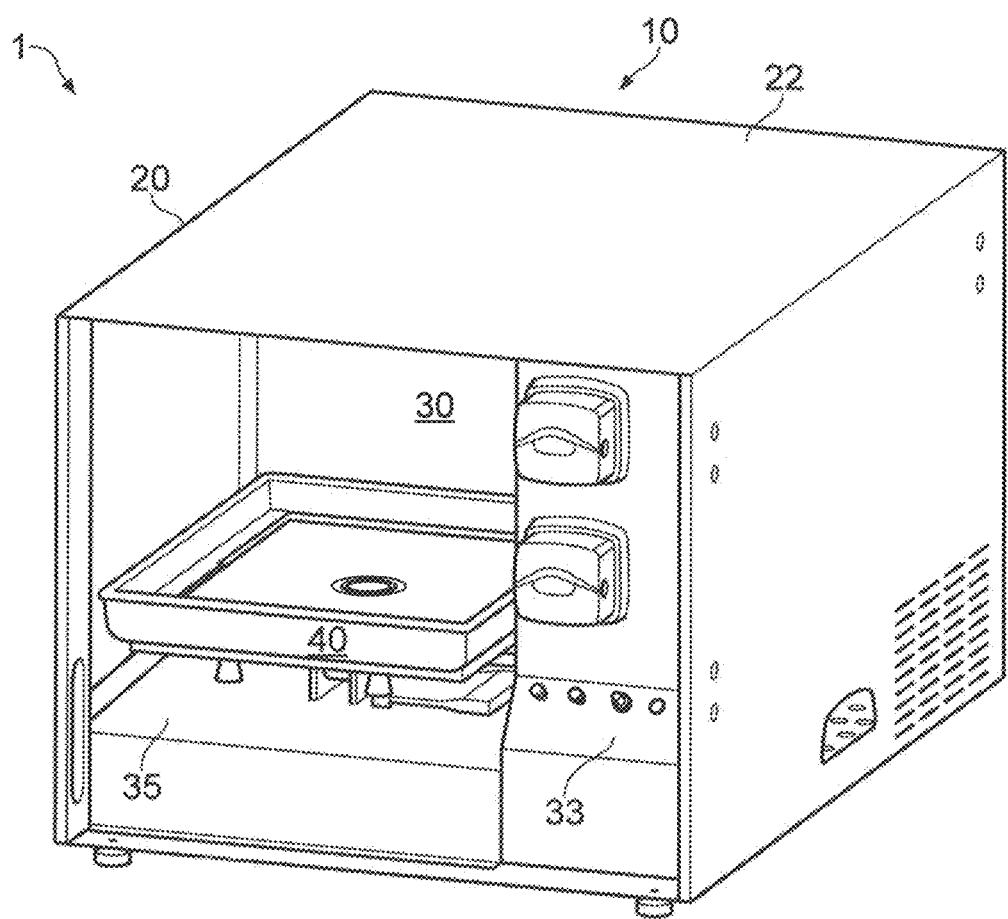
FIG. 2 shows a different pictorial view of the apparatus shown in FIG. 1.

FIG. 2 is a different view of the instrument 10 shown in FIG. 1, with the door 25 and bag rack removed 50, in order to show the remaining parts of the instrument more clearly.

Figure 3:
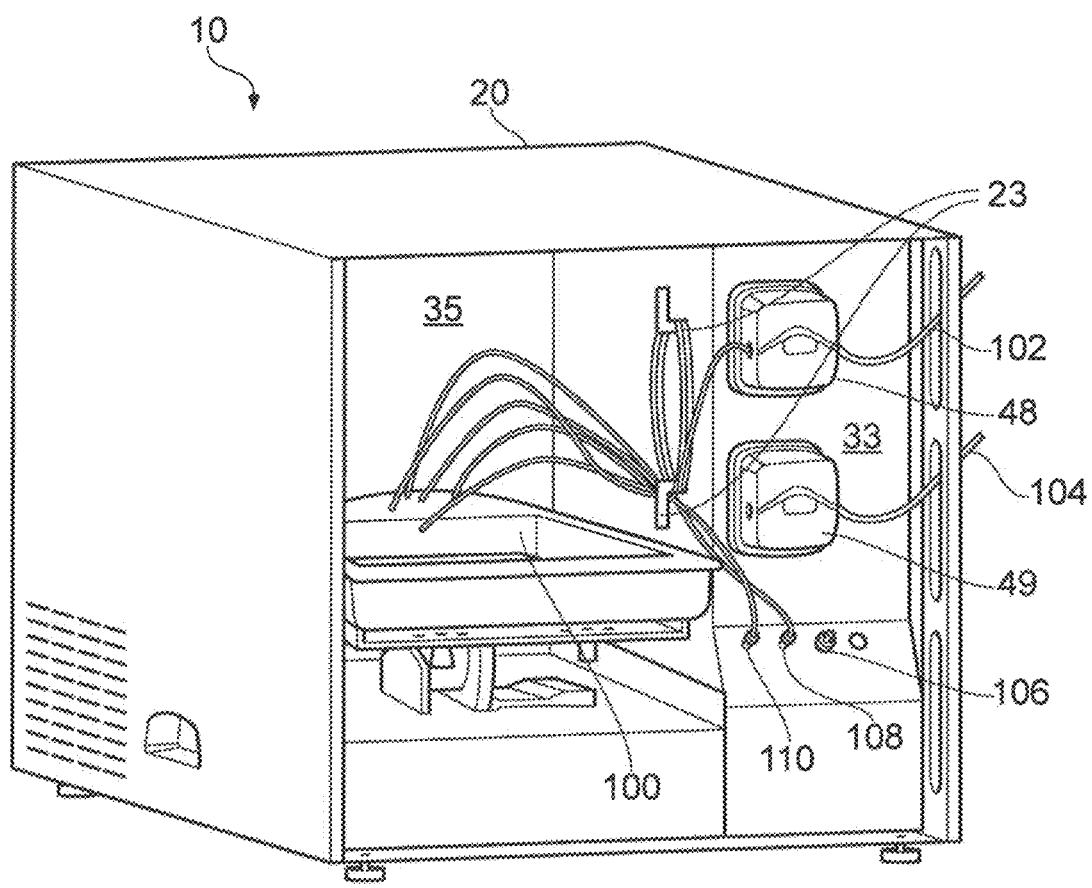
FIG. 3 shows another pictorial view of the apparatus shown in FIG. 1, including a bioreactor loaded inside the apparatus.

FIG. 3 shows the instrument 10 of FIGS. 1 and 2, but loaded with a bioreactor 100, in this instance, in the form of a flexible bag 100, as well as various paths linking the bioreactor to the instrument, including: a fluid supply conduit 102 feeding the bioreactor with a known mixture of fluids to promote cell growth via the peristaltic pump head 48, a fluid removal conduit 104 for drawing off fluids from the reactor for the purpose of removing waste components expressed by cells in the bioreactor via a filter incorporated in the bag 100 and via the peristaltic pump head 49; a gas feed conduit 106; and paths, for example electrically conductive paths 106, 108 and 110 for example electrical wires, for various sensors within or adjacent the bioreactor, for example a pH sensor, and a dissolved oxygen (DO) sensor. The conduits and paths can be kept in place by one or more hangers 23.

Figure 4:
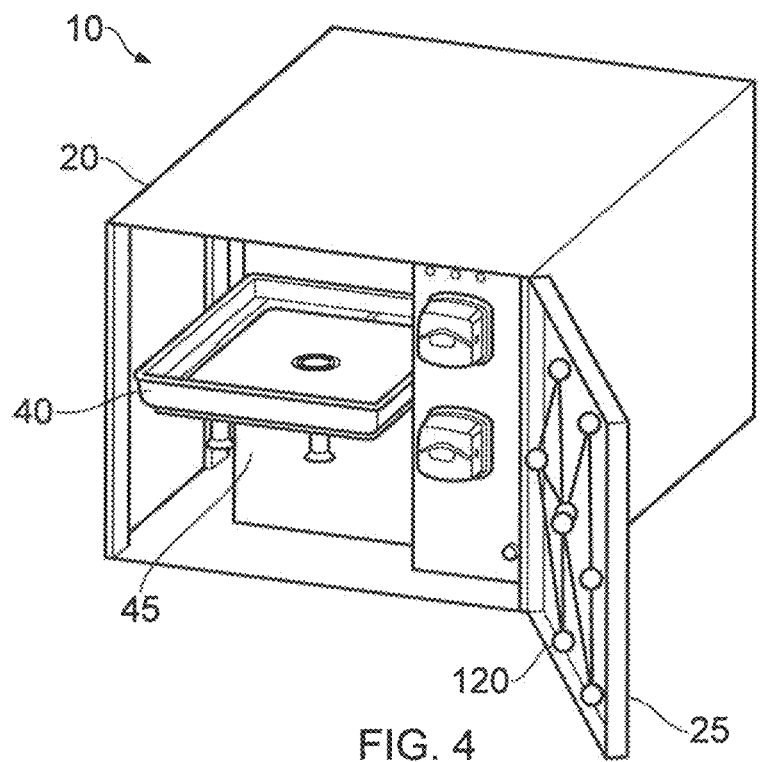
FIGS. 4 and 5 show two pictorial views of a further embodiment of biomanufacturing apparatus, in different configurations.
Figure 5:
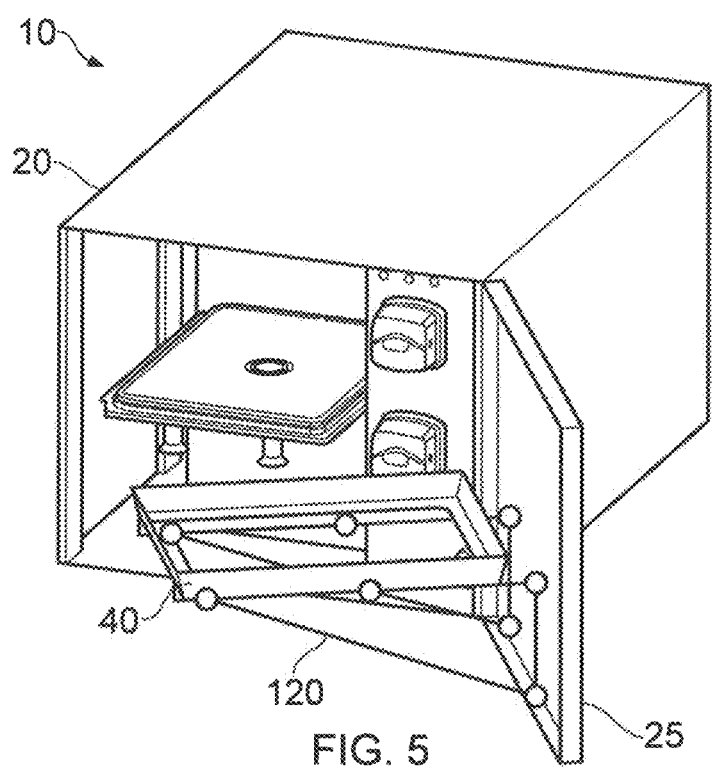

FIGS. 4 and 5 show an embodiment of the instrument 10 including the door 25. The tray 40 in this embodiment is removable from the tray support 45 by sliding motion and can rest on a collapsible stand 120, in turn hung on the hinged door 25. In use, the door 25 can be opened, the stand 120 can be dropped down, and the tray 40 (without or without a bioreactor in place) can be slid away from the support 45 and manually moved onto the stand. It will be noted that the tray 40 has an open mid-section. This open section accommodates a bioreactor, which has clips that clip onto the tray 40 sides so that the bioreactor does not fall through the middle of the tray. Returning the tray full or empty back into the chamber 30, allows the frame 120 to be folded away and the door 25 to be closed shut.

Figure 6A:
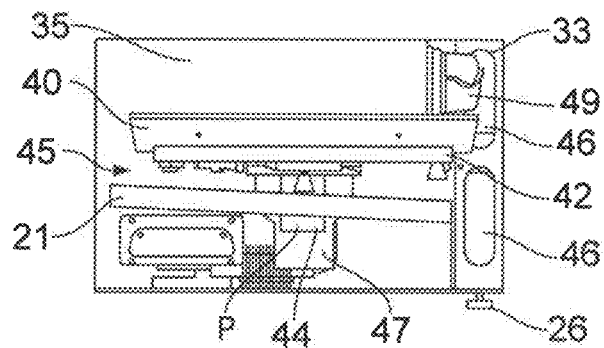
FIGS. 6a, 6b, 6c and 6d show a partial sectional view of the apparatus shown in FIGS. 1 and 2.
Figure 6B:
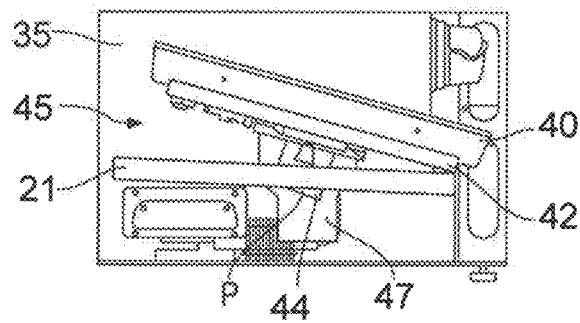
Figure 6C:
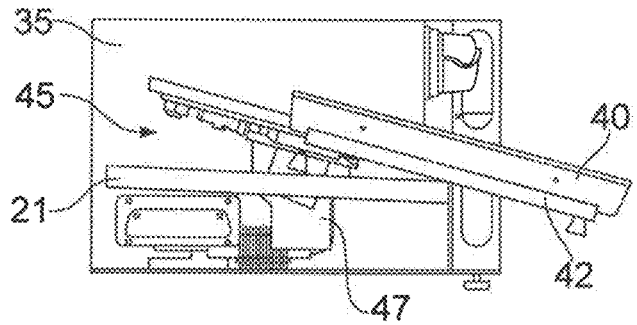
Figure 6D:
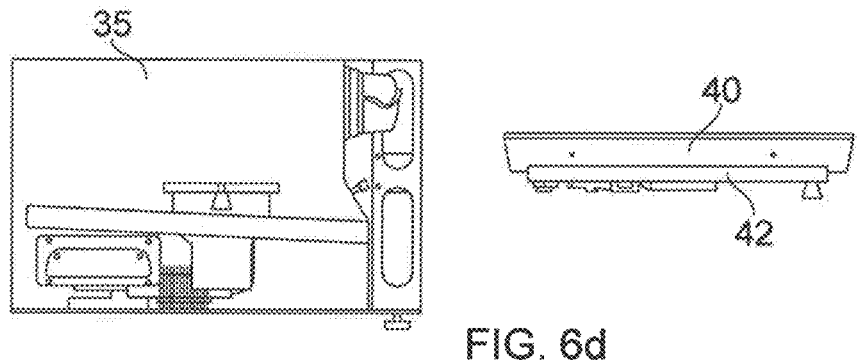

FIGS. 6a, 6b, 6c and 6d each show a sectional view of the main chamber 35 illustrated in FIGS. 1 to 3, and the components housed therein. Those components include the removable tray 40 and the rocking tray support 45. The tray support 45 is formed from an electrically heated plate 42 which is in direct contact with the bottom of a bioreactor in use, a pivotable plate holder 44 which releasably holds the heated plate and an electrical stepper motor driving rocking mechanism 47 which moves the plate holder 44 back and forth about a pivot axis P below the tray 40 through a predefined angle of about 25-35 degrees. The support 45 is controllable in use so that it stops in any position, but in particular in the forward slopping position shown in FIG. 6b, which enables the tray 40 and plate 42 to be slid forward together whilst the plate holder 44 stays in position, to a new position as illustrated in FIG. 6c, where the tray is more readily accessible for loading or unloading rather than having to remove it as shown in the embodiment of FIGS. 4 and 5. In the position shown in FIG. 6c the conduits and paths between the bioreactor and the instrument, as mentioned above, can be connected or disconnected more easily. The tray 40 and plate 42 can be removed completely as shown in FIG. 6d, for example, for cleaning purposes. A cover plate 21 protects the motor and other electrical parts.

Figure 7:
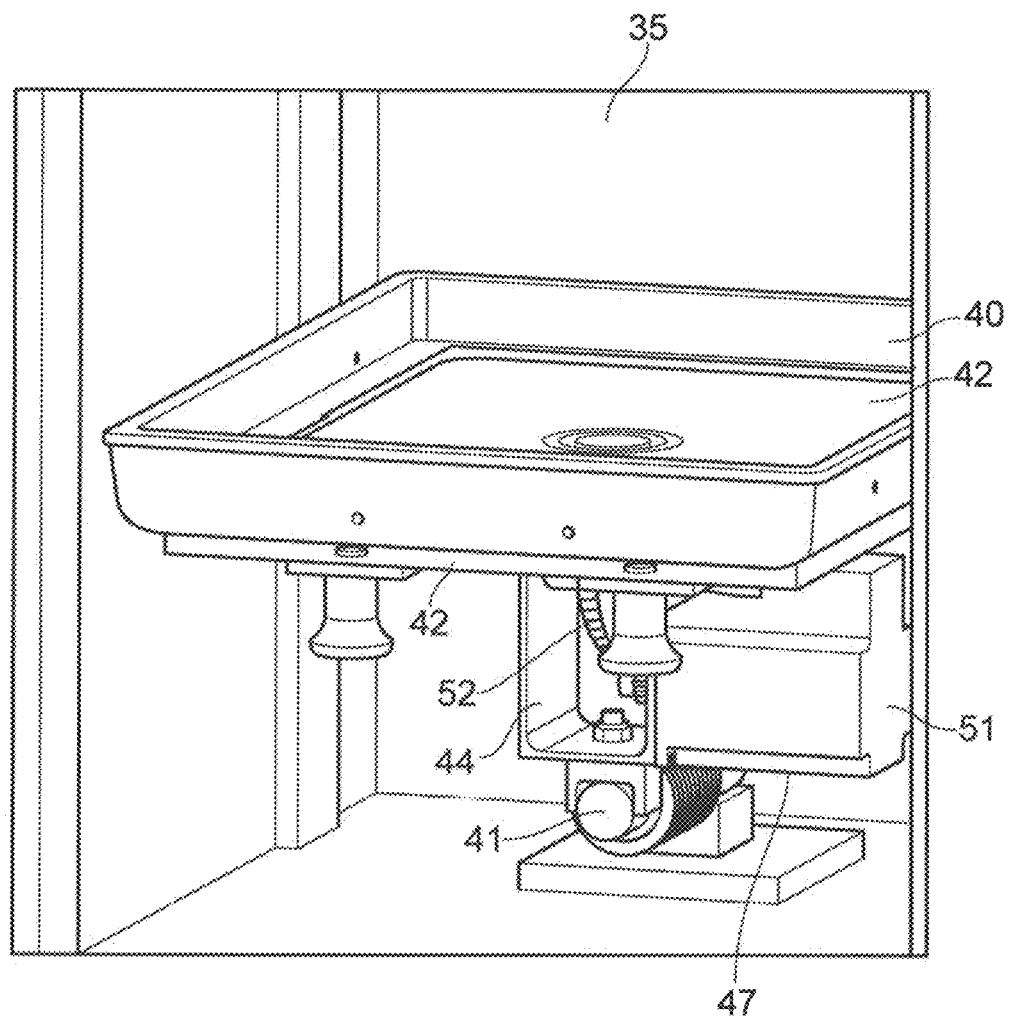
FIG. 7 shows an enlarged partial view of the apparatus shown in FIGS. 1 and 2.

FIG. 7 shows the rocking mechanism in more detail view from the front, door, side of the instrument looking into the main chamber 35 with the cover plate 21 removed. A stepper motor 51 of the rocking mechanism 47 is shown as well as a reduction pinion gear pair 52 driven by the stepper motor and driving the plate support 44 to rotate back and forth. In this view a load sensor, in the form of a load cell 41 is visible which in use is used to measure the quantity of fluid added or removed from the bioreactor, and cell culture control.

Figure 7A:
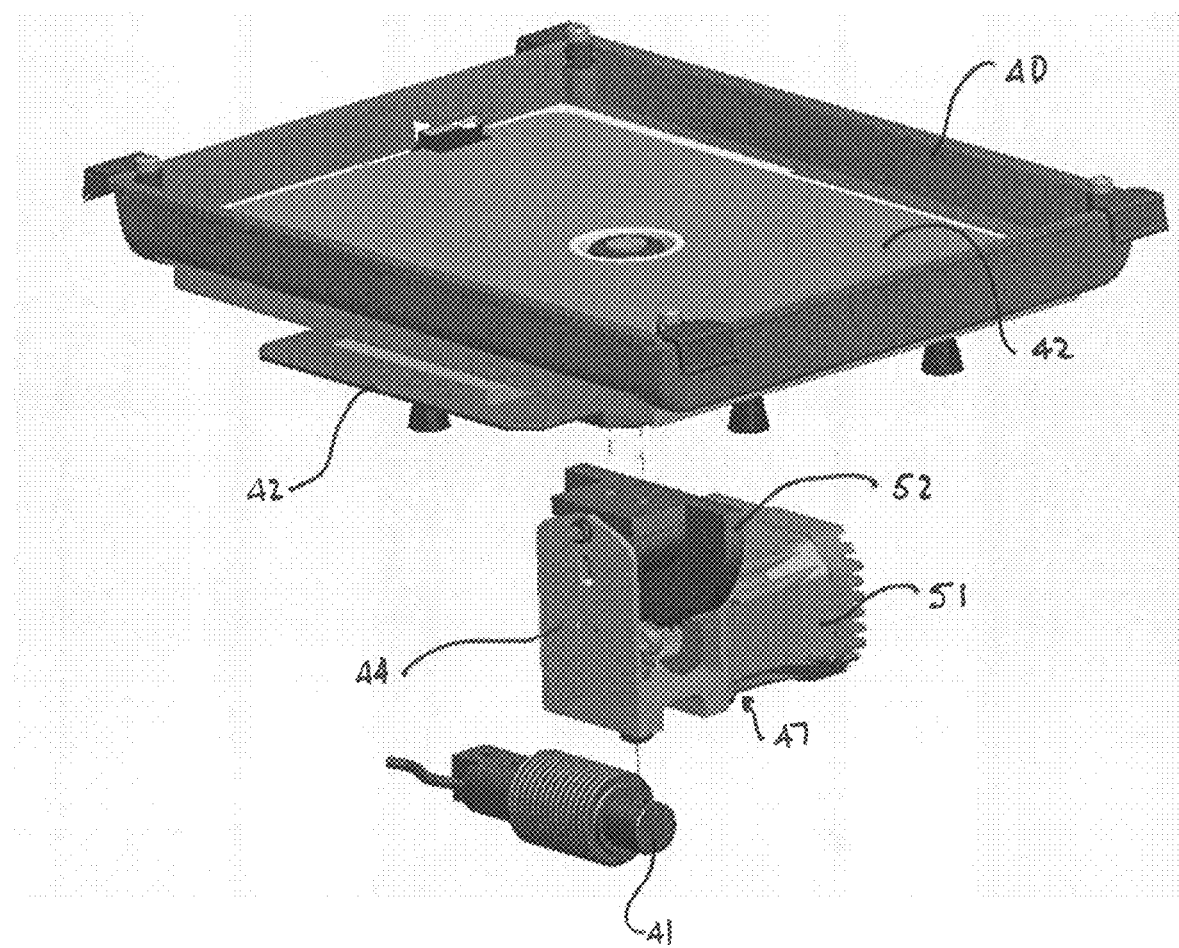
FIG. 7a shows an exploded view of the apparatus shown in FIG. 7.

FIG. 7a shows the features of FIG. 7 but exploded. The mass change measurement system consists of a single load cell 41 mounted to support the cell bag tray 40 and the mechanism 47 that rocks that tray 40. The load cell 41 is a mechanical strain sensor which changes resistance with strain. However other strain sensor could be used, for example optical strain sensors. Since only the drive assembly and the rocking platform are mounted over the load cell, the dead load is significantly reduced. The load cell is completed isolated from the exterior and hence is not affected by any side-forces that act on the apparatus. In use the tray 40 can come to rest in a horizontal position as shown in FIG. 7, before a load measurement is taken. However, it is also envisaged that 'in use' measurements can be taken, i.e. measurements taken whilst the tray 40 is rocking. In that latter case an average weight can be determined, and compared with previous averages, to obtain a measurement of weight increase or decrease. The term 'average' is intended to encompass arithmetic mean, median, mode, range or aggregate loading.

With this weight measurement arrangement, similar apparatus can be stacked one on top of another. This stacking would not be possible if the load cells are mounted on the apparatus feet because then the apparatus at the bottom of the stack will be measuring the weight of the upper apparatus also. Another advantage of having the load cell isolated from the apparatus feet is that the instrument need not be leveled each time before use. In the current bioreactors, the user spends considerable time and effort in levelling the instrument. The weight measurement system of the present embodiment rests on the perfectly machined surface and always sees 100% of the load mounted on it. In traditional bioreactors, each load cell sees a different percentage of the entire instrument weight and the user has to level the instrument so that the percentage of load seen by each load cell is between 25%-30%. A major advantage is however the improved accuracy and sensitivity of the present single load cell configuration. For each additional load cell the accuracy gets poorer by a factor of $\sqrt{n}$ where n is the number of load cells. The accuracy of the single load cell configuration is therefore theoretically better than a four load cell configuration by a factor of 2. This is a key benefit when the bioreactor is used for a low volume cell expansion process.

The modular tray design and a tray eject feature of the apparatus is more fully described in co-pending application IN201611015089 filed 29 Apr. 2016. During the entire cell expansion process, there is a need to take daily samples of the cell culture to monitor the progress of the cell expansion. For taking samples, the instrument door is opened to access the cell bag on the tray. The tray comes to a stop in an inclined position which ensures that the contents inside the cell bag come near the sampling port of the cell bag by gravity. When the sampling is carried out by the user, there is a chance that some weight is transferred on to the rocking platform and therefore to the load cell. To prevent any damage to the load cell due to overloading, the weight measurement system can have a load cell overload protection which supports the ejected tray or an inclined tray at the bottom and the load cell is isolated from taking any load at these conditions of the tray. In other words, when the tray 40 is fully inclined as shown in FIG. 6b, that arrangement can be modified such that the lowermost edge of tray 40 can rest on the floor of the chamber 35. The apparatus may also have an alarm for overload protection for any unforeseen circumstances at any point of time during the entire cell expansion process. The weight measurement system also has an auto alignment feature to receive the ejected tray back into the correct position to prevent any misalignment. The user only needs to push the ejected tray back till an audible click is heard conveying that the tray is aligned and in position. The user can thus be assured that the tray is safe to start rocking.

Figure 8:
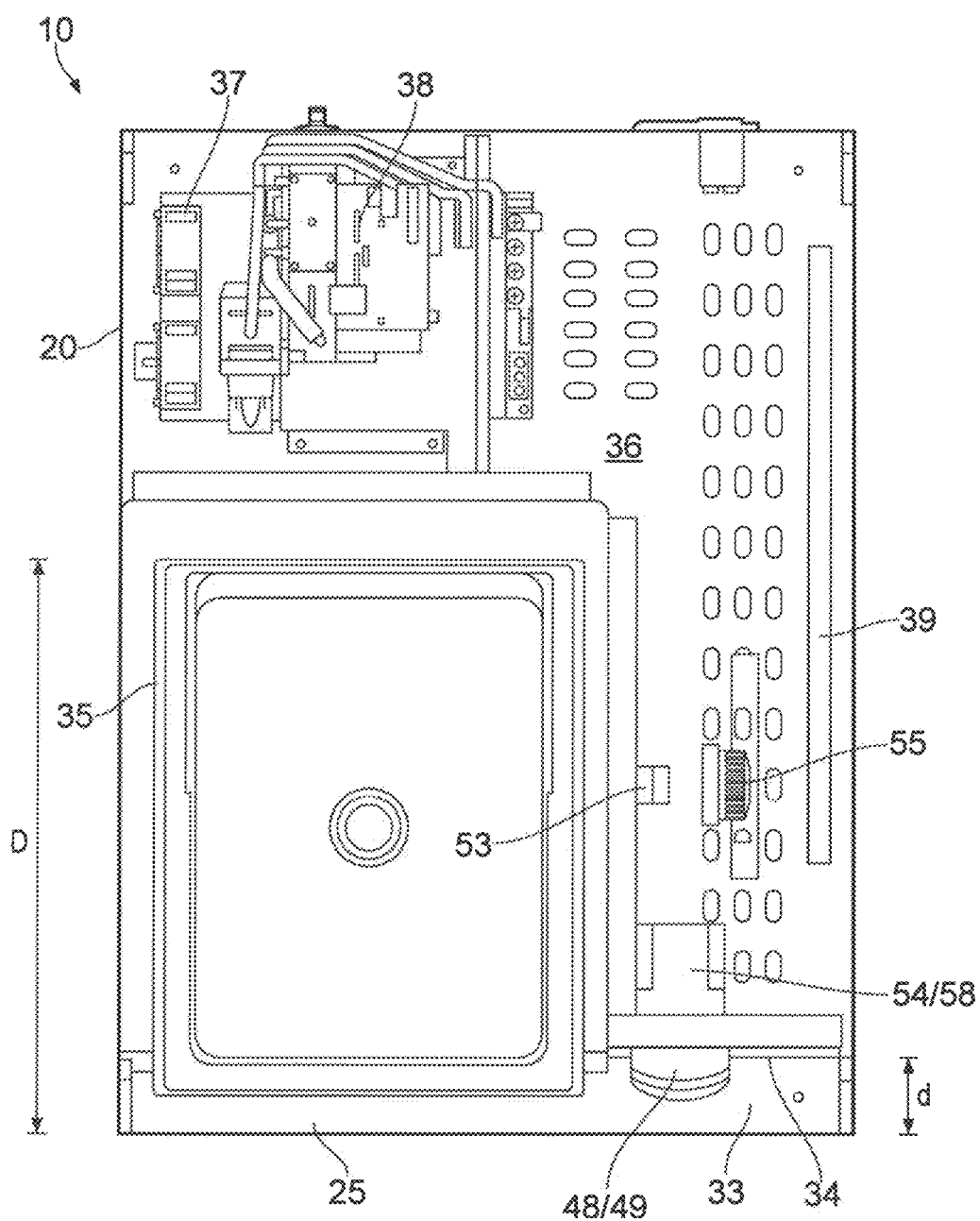
FIG. 8 shows a sectional plan view of the apparatus shown in FIGS. 1 and 2.

FIG. 8 shows a sectional view through the instrument 10 looking down such that the main chamber 35 is visible having a depth D from front to back, as well as the antechamber 33, which has a much shallower depth d. In the remaining region 36 of the housing is separated from the chambers 35/33 and encloses electrical and electronic control components which are kept way from possible leaks from the bioreactor and can be kept at lower temperature than the main chamber, so that electrical parts will have a longer life. In addition, cleaning of the electrical parts can be avoided because they are separated from the chambers 35/33. In more detail, those electrical/electronic components include a power supply 37, a perfusion gas supply control unit 38, a control circuit board 39, a chamber air heater 53, pump head 48/49 drive motors 54/58, a single board computer 55 and various connecting wires and conduits not shown.

Figure 9:
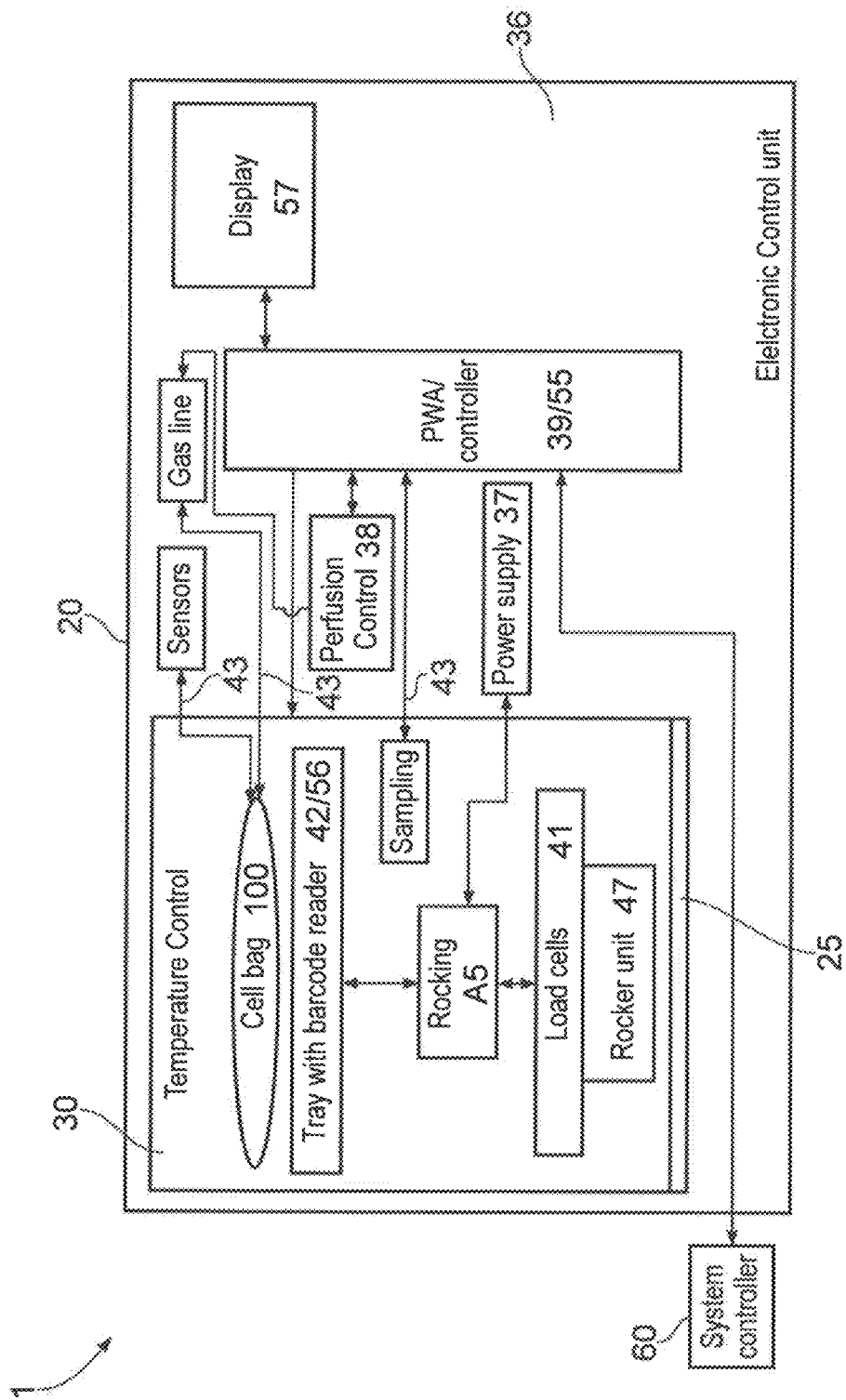
FIG. 9 shows a schematic representation of the functioning of the apparatus shown in FIGS. 1 and 2.

FIG. 9 shows schematic block diagram of the functioning of the instrument 10, with references relating to the physical components mentioned above and illustrated in the previous Figures. In use the flexible bag bioreactor 100 (cell bag) is preferred, and is loaded into the chamber 30 as detailed above. Connections 43 are made and the door 25 is closed. The tray 42, in this embodiment includes a bar code reader 56, to reader a bar code from the bag and relay the identity of the bag to a controller 39/55. Other identification means are possible, for example an RFID transducer could be used, embedded in the cell bag 100. The identity of the bag will determine the appropriate cell culture regime, and additional, external information can be sought by the controller via a system controller 60, for example the target cell density required. Having determined the appropriate cell culture regime, the controller will, typically, control the temperature external to the bag, and optimise the parameters inside the bag. These parameters will vary during the cell culture period, i.e. over a period of up to 28 days, but typically 7 to 21 days. Thus the controller will monitor and adjust the internal pH of the cell culture, the dissolved oxygen content of the fluid in the bag, the weight of the bag to determine the amount of fresh fluid introduced and the amount of waste fluid withdrawn from the bag. Sampling of these parameters and the cell density is performed automatically. A continuous perfusion regime is preferred although other known regimes, such as a fed batch regime could be used. Conveniently, a display 57 is incorporated into the door 25, and the door includes a window which is darkened to reduce light entering the chamber or has a shutter, openable to view the chamber 30 through the window, but closable to reduce or exclude light in normal operation of the instrument.

In use the instrument will function as a stand-alone system using the display 57 to output status information, along with other stand-alone instruments where plural instruments are employed, meaning that no external control is required for the operation of the instrument or instruments. However, it is possible that the system controller 60 can be used, will function either to simply supply information relating to the requirements of the cell bag loaded in the instrument, or additionally monitor plural instruments, or with suitable software, to monitor and control each instrument, so that internal instrument control is dominant. The then subordinate controller 39/55 of each instrument can take back instrument control if communication with the system controller is lost. The communication between the instruments and the system controller is preferably a system BUS link for example a universal serial bus of know configuration, but a wireless link is possible, for example as specified by IEEE802.11 protocols operating at 0.9 to 60 GHz. It is envisaged that each instrument will be automatically recognised by software running on the system controller, without the need for any user input.

Once the cell culture is complete, as determined by sampling and or cell bag weight, it is removed from the instrument and used for its intended purpose, for example autologous cell therapy. Where it is the biomolecules produced by cultured cells that is of interest these can be removed when the cell bag is emptied, or they can be removed from the filtrate extracted from the bag during culturing. The chamber 30 is easily cleaned ready for the next bag to be introduced, with minimal down-time. Thus it is apparent that the instrument described above allows convenient loading and unloading of disposable bioreactors, and can be closely spaced in stacked rows so that the density of instruments is about 4 to 6 per metre squared when viewed from the instruments' front faces. A typical bioreactor 100 for use with the instrument 10, will be small by present day standards, i.e. approximately 50 millilitres and 2500 millilitres, and so the system described above is a small scale system, having multiple cell culture instruments, which are each readily accessible and controllable, and optimise the available space.

Although embodiments have been described and illustrated, it will be apparent to the skilled addressee that additions, omissions and modifications are possible to those embodiments without departing from the scope of the invention claimed.

The invention claimed is:

1. A biomanufacturing apparatus comprising a housing including top and bottom faces which allow stacking of plural housings,
   an access door at a front side of the housing,
   a substantially enclosed bioreactor chamber inside the housing accessible via the access door, and
   a further substantially enclosed region inside the housing containing at least one of electrical parts and electronic control components,
   wherein the chamber includes:
   a tray for supporting a bioreactor, and
   a tray support including a mechanism for rocking the tray in use, the tray support further including a load cell to determine changes in a mass load on the tray, wherein the mechanism for rocking the tray is configured to move a plate holder back and forth about a pivot axis below the tray,
   wherein the tray support further includes a sliding portion for automatically sliding the tray at least partially out of the chamber via an open door, the sliding portion being arranged such that when inclined by the mechanism for rocking, a portion of the mass load on the tray is reacted by the housing and therefore is not transmitted through the load cell, wherein the sliding portion is mounted between the tray and the mechanism for rocking the tray that is located above the load cell.

2. The apparatus of claim 1, wherein: the load cell is mounted to the floor of the chamber; the mechanism for rocking is mounted on the load cell; and the tray is mounted on the mechanism for rocking.

3. The apparatus of claim 1, wherein: the chamber has a main chamber region for housing the tray and the tray support, and an antechamber region shallower in depth relative to the access door than the main chamber region, the antechamber region including a panel to which is mounted at least one fluid pump device such that fluid handling portion(s) of the at least one fluid pump device project beyond the panel into the antechamber region.

4. The apparatus of claim 3, wherein at least one connection is mounted to the panel, said at least one connection being adapted for removably connecting one or more of: a gas conduit; a pH sensor connection path; and a dissolved oxygen sensor connection path.

5. The apparatus of claim 1, wherein the tray is at least one of slidable relative to and removable from, the tray support.

6. The apparatus of claim 5, wherein the access door includes a further tray support for supporting the tray on the access door when the access door is open, the further tray support being collapsible to allow the access door to close.

7. The apparatus of claim 1, wherein the load cell is a mechanical strain sensor, operable to determine the changes in the mass load supported on the tray.

8. The apparatus of claim 1, further including a bioreactor heater mounted at the tray for conductive heating of the bioreactor, and a chamber air heater for convective heating the gaseous atmosphere in the chamber, each heater being controlled by a temperature control.

9. The apparatus of claim 1, wherein said top and bottom faces are generally flat and include height adjustable feet.

10. The apparatus of claim 1, further including a support external to the housing to one side of the access door for supporting at least one of consumable materials and fluid products.

11. The apparatus of claim 4, further including the bioreactor in the form of flexible bag supported on the tray, said flexible bag including fluid conduits passing via pump heads connected or connectable to connections.

12. The apparatus of claim 1, wherein the bioreactor has a capacity of between approximately 50 millilitres and 2500 millilitres.

13. The apparatus of claim 1, wherein the tray or the tray support includes a reader for recognizing the identity of the bioreactor mounted on the tray.

14. The apparatus of claim 1, wherein the chamber, with the access door closed, reduces or substantially excludes visible light.

15. The apparatus of claim 1, wherein the access door includes a status display viewable from at least one of the outside of the access door and a window for viewing the chamber.

16. A biomanufacturing system, comprising, a plurality of stacked biomanufacturing apparatus of claim 1, in data communication with a central computer including software operable to at least one of monitor the status of and control one or more of the apparatus.

17. The apparatus of claim 10, wherein the at least one of consumable materials and fluid products comprises at least one of bagged waste and biomolecules.

* * * * *